United States Patent [19]

Foglio et al.

[11] 4,085,113
[45] Apr. 18, 1978

[54] PROCESS FOR THE PREPARATION OF AZETIDINONE-THIAZOLINE PRECURSORS FOR CEPHALOSPORIN SYNTHESIS

[75] Inventors: Maurizio Foglio; Ugo Scarponi, both of Milan; Federico Arcamone, Nerviano (Milan), all of Italy

[73] Assignee: Societa' Farmaceutici Italia S.p.A., Milan, Italy

[21] Appl. No.: 598,260

[22] Filed: Jul. 23, 1975

[30] Foreign Application Priority Data

Oct. 3, 1974    United Kingdom ............... 42859/74

[51] Int. Cl.² ........................................... C07D 513/04
[52] U.S. Cl. .............................................. 260/306.7 C
[58] Field of Search ................................. 260/306.7 C

[56] References Cited

U.S. PATENT DOCUMENTS

| | | | |
|---|---|---|---|
| 3,594,389 | 7/1971 | Cooper | 260/306.7 C |
| 3,862,164 | 1/1975 | Cooper | 260/306.7 C |
| 3,862,181 | 1/1975 | Davis et al. | 260/243 C |
| 3,900,487 | 8/1975 | Underwood et al. | 260/306.7 C |

OTHER PUBLICATIONS

Burwell, Chem. Rev., vol. 54, (1954), p. 626ff.
Hartung et al., Org. Reactions, vol. VII, (1953), pp. 267, 268.

McOmie, Protective Groups in Organic Chemistry, (1973), pp. 99 and 119.

Primary Examiner—Raymond V. Rush
Assistant Examiner—David E. Wheeler
Attorney, Agent, or Firm—Oblon, Fisher, Spivak, McClelland & Maier

[57] ABSTRACT

A process for the preparation of azetidinone-thiazoline precursors for cephalosporin synthesis. Said precursors are obtained by reducing by means of zinc dust in the presence of aqueous acetic acid a compound of formula

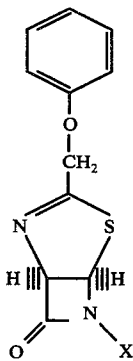

1 Claim, No Drawings

PROCESS FOR THE PREPARATION OF AZETIDINONE-THIAZOLINE PRECURSORS FOR CEPHALOSPORIN SYNTHESIS

This invention relates to the preparation of azetidinone-thiazoline precursors for cephalosporin synthesis. The precursors have the general formula (II) below and may be used in the synthesis of derivatives of 7-aminocephalosporanic acid (7-ACA) and 7-aminodesacetoxy-cephalosporanic acid (7-ADCA).

The invention comprises reducing a compound of the general formula (I) below to a compound of the general formula (II) below using zinc dust in the presence of aqueous acetic acid.

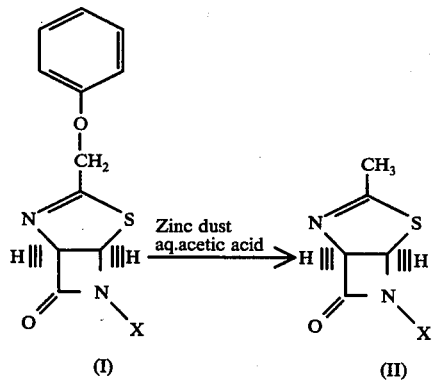

In the above formulae (I) and (II), X represents a hydrogen atom or a group of the structure

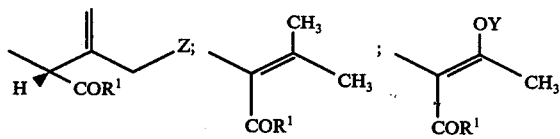

in which $R^1$ is a hydroxy group, an alkoxy group having from 1 to 4 carbon atoms, a 2',2',2'-trichloroethoxy, a benzyloxy, p-methoxybenzyloxy, p-nitrobenzyloxy, benzhydryloxy, triphenylmethoxy, phenacyloxy, p-halophenacyloxy, phthalimidomethoxy, acyloxymethyloxy, acylamidomethyloxy, free or protected hydrazino or free amino group, or an amino group that is substituted by one or more alkyl groups having from 1 to 4 carbon atoms, cycloalkyl groups having from 5 to 8 carbon atoms, phenyl groups or mononuclear heterocyclic groups;

Z is a hydroxy group, an —O-Alkyl, —S-Alkyl or —O-CO-Alkyl group in which the alkyl component contains from 1 to 4 carbon atoms, an —OCONH$_2$, —N$_3$, —NH$_2$ or —S-aryl group or a —S-mononuclear heterocyclic group in which the heterocyclic component contains one or more nitrogen or sulphur atoms; and Y is a hydrogen atom or an alkyl group having from 1 to 4 carbon atoms.

The reduction reaction is preferably carried out in the cold in the presence of an excess of zinc dust and the resulting product may be recovered and purified according to the conventional procedures for such products.

The following Examples illustrate this invention:

EXAMPLE 1

Methyl-α-isopropenyl-3-methyl-1α,5α-4-thia-2,6-diazabicyclo[3,2,0]-2-heptene-6-acetate-7-one (IV)

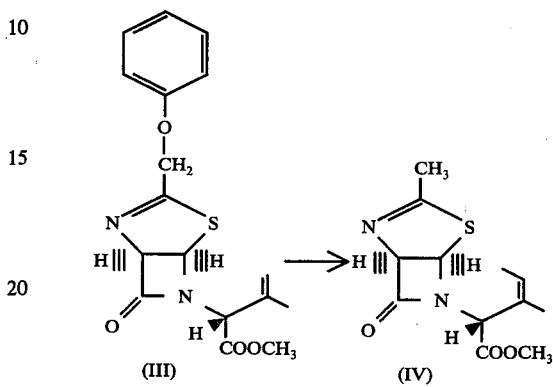

A cooled solution of methyl-α-isopropenyl-3-phenoxymethyl-1α,-5α-4-thia-2,6-diaza-bicyclo[3,2,0]-2-heptene-6-acetate-7-one, (III), (3.0 g), in 25 ml of 90% acetic acid was treated with an excess of zinc metal dust and stirred for 1 hour. After addition of water (100 ml) and ethyl acetate (100 ml), the organic layer was separated and washed first with water, then with aqueous NaHCO$_3$ and finally with water again. The organic solution was dried over anhydrous Na$_2$SO$_4$, the solvent evaporated and the residue chromatographed (silica gel; benzene/ethyl acetate, 95/5) to give 1.8 g of a product having the structure IV above:

IR (CHCl$_3$) : 1762 cm$^{-1}$ (C=O β-lactam)

1740 cm$^{-1}$(C=O ester)

NMR (CDCl$_3$) : 1.88δ (m, 3H, $CH_3-\overset{|}{C}=N-$)

2.28δ (m, 3H, $CH_3-\overset{|}{C}=\overset{|}{C}-$), 3.78δ (s, 3H, CH$_3$O—), 4.88 and 5.00δ (two m, 2H, =CH$_2$), 5.15δ (q, J∼1Hz, 1H, $-N-CH(CO-)\overset{|}{C}=$), 5.96δ (m, 2H, β-lactam protons).

EXAMPLE 2

Methyl-β-acetoxyisopropylidene-3-methyl-1α,5α-4-thia-2,6-diaza-bicyclo[3,2,0]-2-heptene-6-acetate-7-one (VI)

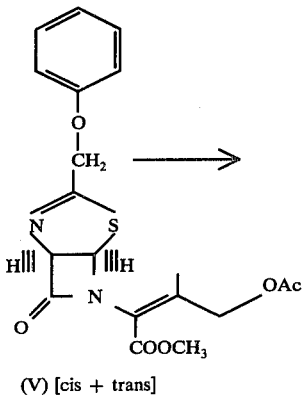

(V) [cis + trans]

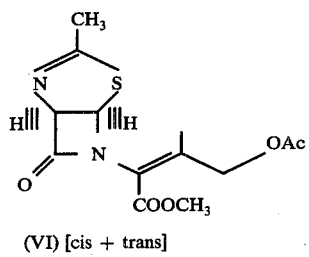

(VI) [cis + trans]

A cooled solution of methyl-α-acetoxyisopropylidene-3-phenoxymethyl-1α,5α-4-thia-2,6-diaza-bicyclo[3,2,0]-2-heptene-6-acetate-7-one, (V), (1.0 g) in 10 ml of 90% acetic acid was treated with an excess of zinc metal dust and stirred for 90 minutes. Water (100 ml) and ethyl acetate (100 ml) were added and the organic layer was separated and washed with water, then with aqueous NaHCO₃ and then again with water. The solvent was evaporated in vacuo and the residue chromatographed (silica gel; benzene/ethyl acetate 95/5) to give 0.450 g of a product with the general formula VI above as a mixture of two stereoisomers.

NMR (CDCl₃): 1.89 δ (s, 1H, 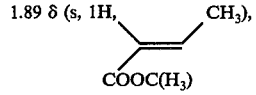), 2.10 δ (s, 3H, CH₃—CO—), 2.22 δ (s, 2H, 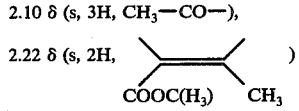)

2.33 δ (s, 3H, CH₃—C=N), 3.82 δ (s, 3H, CH₃—O—), 4.68 δ (m, 1H, 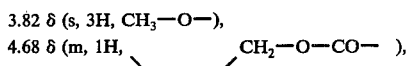), 5.15 δ (m, 1H, 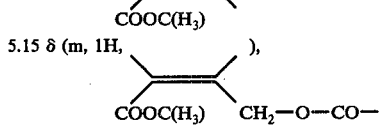),

EXAMPLE 3

α-Isopropylidene-3-methyl-1α,5α-4-thia-2,6-diaza-bicyclo[3,2,0]-2-heptene-6-acetic acid-7-one (VIII)

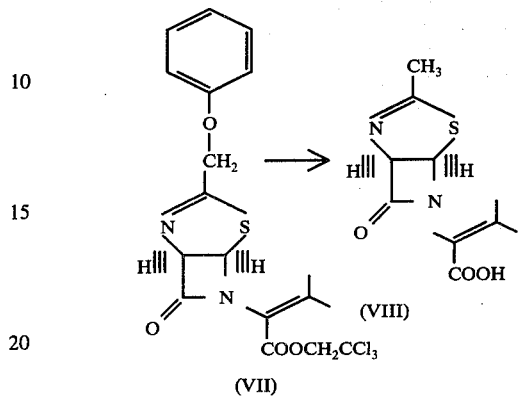

A cooled solution of 2.0 g of 2',2',2'-trichloroethyl-α-isopropylidene-3-phenoxymethyl-1α,5α-4-thia-2,6-diaza-bicyclo[3;2,0]-2-heptene-6-acetate-7-one, (VII), in 20 ml of 90% acetic acid was treated with an excess of zinc metal dust and stirred for 90 minutes. Water (100 ml) and ethyl acetate (100 ml) were added and the organic layer was separated and washed with water (3 × 50 ml). The organic solution was carefully neutralized with aqueous NaHCO₃ and the aqueous layer was separated and acidified with 0.1 N HCl. The product was immediately extracted with ethyl acetate. Evaporation of the solvent gave 0.800 g of a product of the general formula (VIII) above.

IR (CHCl₃) : 1760 cm⁻¹ (C=O β-lactam) 1690 cm⁻¹ (C=O acid)

NMR (CDCl₃) : 1.95 δ (s, 3H, CH₃—C=N), 2.31 and 2.34δ (two s, 6-H, (CH₃)₂C=), 6.02δ (m, 2H, β-lactam protons), 8.77 δ (s, 1H, COOH).

What we claim is:

1. A process for the preparation of azetidinonethiazoline precursors for cephalosporin synthesis of the formula:

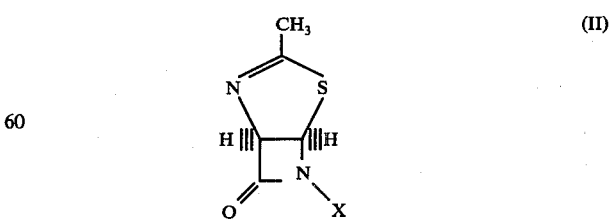

wherein X is a member selected from the group consisting of a hydrogen atom and of a group of the structure:

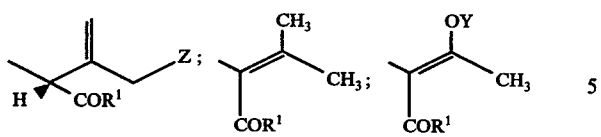

in which R¹ is a member selected from the group consisting of a hydroxy group, an alkoxy group having from 1 to 4 carbon atoms, a trichloroethoxy, a benzyloxy, p-methoxybenxyloxy, p-nitrobenzyloxy, benzhydryloxy, triphenylmethoxy, phenacyloxy, p-halophenacyloxy, phtalimidomethoxy, acyloxymethyloxy, acylamidomethyloxy; Z is a member selected from the group consisting of hydrogen, an —O-alkyl, or —O—CO-alkyl group in which the alkyl component contains from 1 to 4 carbon atoms, and Y is a member selected from the group consisting of a hydrogen atom and an alkyl group having from 1 to 4 carbon atoms, which comprises the steps of reducing a compound of formula:

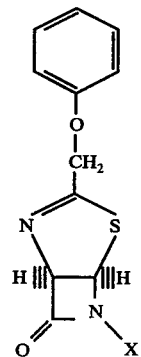

wherein X is defined above by means of zinc dust in the presence of aqueous acetic acid at a temperature and for a time sufficient to convert the phenoxymethyl group to a methyl group while retaining the 2,3 double bond of the thiazoline ring, recovering the product so obtained and purifying it.

* * * * *